United States Patent [19]
Reidenberg et al.

[11] Patent Number: 5,939,098
[45] Date of Patent: *Aug. 17, 1999

[54] CANCER TREATMENT WITH TEMOZOLOMIDE

[75] Inventors: Pascale Reidenberg, Westfield, N.J.; Margaret H. Dugan, Woodside, N.Y.

[73] Assignee: Schering Corporation, Kenilworth, N.J.

[ * ] Notice: This patent is subject to a terminal disclaimer.

[21] Appl. No.: 08/902,380

[22] Filed: Jul. 29, 1997

Related U.S. Application Data

[60] Provisional application No. 60/025,748, Sep. 19, 1996.

[51] Int. Cl.⁶ ..................................................... A61K 31/33
[52] U.S. Cl. ............................................ 424/451; 514/183
[58] Field of Search ..................................... 424/464, 451; 514/183

[56] References Cited

U.S. PATENT DOCUMENTS 5,731,304  3/1998  Baer et al. .

FOREIGN PATENT DOCUMENTS

943/15615  7/1994  WIPO .

OTHER PUBLICATIONS

Newlands et al., The Charing Cross Hospital Experience with Temozolomide in Patients with Gliomas, European Journal of Cancer, vol. 32A, No. 13, pp. 2236–2241, Dec. 1996.
Newlands, *British J. Cancer*, 65(2), 287–292 (1992).
Bleehen et al, *J. Clinical Oncology*, 13(4), 910–913 (1994).
O'Reilly et al, *European J. cancer*, 29A, 940 (1993).
Stevens et al, *J. Medicinal Chem.*, 27, 196–201 (1984).
Wang et al, *J. Chem. Soc.—Chem. Comm.*, 1687–1688 (1994).

*Primary Examiner*—Thurman K. Page
*Assistant Examiner*—Brian K. Seidleck
*Attorney, Agent, or Firm*—Palaiyur S. Kalyanaraman

[57] ABSTRACT

There is disclosed a method for treating cancer in a patient in need of such treating comprising administering temozolomide in an amount sufficient to achieve a clinical response wherein the temozolomide is administered more than once per day. Preferred specific dosing schedules are provided.

12 Claims, No Drawings

CANCER TREATMENT WITH TEMOZOLOMIDE

This application claims the benefit of U.S. Provisional Application Ser. No. 60/025,748, filed Sep. 19, 1996.

This invention relates to the treatment of cancer and in particular to the treatment of cancers with Temozolomide.

Temozolomide is known for its anti-tumor effects. For example, in one study clinical responses were achieved in 17% of patients having advanced melanoma (Newlands ES, et al. Br J Cancer 65 (2) 287–2981, 1992). In another study a clinical response was achieved in 21% of patients with advanced melanoma (Journal of Clinical Oncology, Vol 13, No. 4 (April), 1995, pp 910–913). Treatment of gliomas in adults with temozolomide is also known (Eur. J. Cancer 1993; 29A:940). Treatment of the following cancers in adults with temozolomide has also been disclosed: metastatic melanoma; high grade glioma, glioblastoma and other brain cancers; lung cancer; breast cancer; testicular cancer; colon and rectal cancers; carcinomas; sarcomas; lymphomas; leukemias; and mycosis fungoides. This invention is predicated on the discovery that the effectiveness of temozolomide for treating cancer can be improved by use of twice, three times, or four times a day dosing, instead of once a day dosing formerly believed to be the only dosing possible with temozolomide.

SUMMARY OF THE INVENTION

This invention may be summarized as a method for treating cancer in a patient in need of such treating comprising administering temozolomide in an amount sufficient to achieve a clinical response wherein the temozolomide is administered more than once per day. Preferred aspects of the invention are administration of temozolomide twice, three times, or four times per day.

DETAILED DESCRIPTION

All references cited herein are incorporated herein by reference.

The term "temozolomide" is intended to mean a compound having the formula:

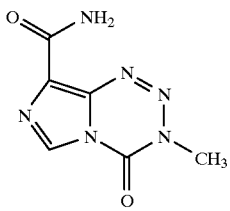

One chemical name for temozolomide is 3,4-dihydro-3-methyl-4-oxoimidazo-[5,1-d]1,2,3,4-tetrazin-8-carboximide. The synthesis of temozolomide is well known. See, for example, Stevens et al., J. Med. Chem, 1984, 27, 196–201 and Wang et al., J. Chem. Soc., Chem. Commun., 1994, pp 1687–1688.

Cancers treatable by this invention may include melanoma; high grade glioma, glioblastoma and other brain cancers; lung cancer; breast cancer; testicular cancer; gastro intestinal cancers including colon, rectal, pancreatic, and gastric cancers, hepatocellular carcinoma; head and neck cancers; prostate cancer, renal cell carcinoma; adenocarcinoma; sarcomas; lymphomas; leukemias; and mycosis fungoides. This invention contemplates treating these cancers and other cancers at any stage from the discovery of the cancer to the advanced stage. The invention includes treatment of the primary cancer and metastases thereof.

A person suffering from cancer may exhibit one or more of the following signs or symptoms:
(a) presence of cancerous tumor,
(b) fatigue,
(c) pain,
(d) decreased performance status from tumor burden, and
(e) the well known symptoms associated with each specific cancer.

To practice the invention, temozolomide is administered to the patient exhibiting one of more of the above signs or symptoms in an amount sufficient to eliminate or at least alleviate one or more of the signs or symptoms. The temozolomide is administered at more than once per day.

Prior to this invention it was generally believed that administering temozolomide to a patient having food in his stomach or to a patient who consumed food too soon before or after administering of the temozolomide would interfere with the bioiavailability of the temozolomide. A fasting of about 8 hours, before administering of temozolomide and 4 hours after receiving temozolomide was believed necessary. Since two twelve-hour fasting periods per day would obviously be unacceptable, it was believed that temozolomide could be administered a maximum of once per day. A food effect interaction study was undertaken and has found that such fasting is not necessary. It was found that food effects the rate of absorption of the compound, but that the effect on the extent of absoption was small (Area Under Curve (AUC) for those fed was about 90% of AUC for those fasted). Therefore long fasting periods before and after administration of temozolomide are not necessary. Dosing with temozolomide more than once per day may improve the effectiveness of the treatment. This is so because increasing the frequency of dosing may deplete the $O^6$-aklylguanine DNA alkyltransferase more effectively and maintain the depletion of this repair enzyme, resulting therefore in better effectiveness of the drug.

The preferred dosage of temozolomide for practicing this invention is a total dose of 500 to 1200 mg/m² of the patient's body surface area, administered over a period of from 2 to 28 consecutive days, more preferable over a period of from 4 to 7 consecutive days, and most preferably over a period 5 consecutive days. Thus if the total dose is to be 1000 mg/m² administered over a period of 5 days, the daily dose for this period would be 200 mg/m². The temozolomide must be administered more than once per day. Preferable dosing regimens would be twice per day, three times per day or four times per day.

Alternatively the temozolomide may be administered for a much longer period at reduced dosage. For example, the temozolomide could be administered more than once daily for up to six weeks at a daily dosage of 50 to 150 mg/m²/day, preferably 75 mg/m²/day. Of course these daily doses are split about evenly into two or more doses to be administered two or more times per day.

Regardless of the total amount of the dosage or the length of the administration period, it may be preferable to administer a larger oral bolus dose for the first dose to achieve a better depletion of the DNA alkyltransferase, followed by a maintenance dose to maintain the depletion. The following examples serve to illustrate, but not limit dosing according to the invention.

EXAMPLE 1

On day 1 administer 200 mg/m² as an initial bolus dose and 12 hours later administer 50 mg/m². On days 2 to 5 administer 50 mg/m² every 12 hours. The total dose is 650 mg/m² over a five-day period.

EXAMPLE 2

On day 1 administer 200 mg/m² as an initial bolus dose and 12 hours later administer 75 mg/m². On days 2 to 5 administer 75 mg/m² every 12 hours. The total dose is 875 mg/m² over a five-day period.

EXAMPLE 3

On day 1 administer 200 mg/m² as an initial bolus dosage and 12 hours later 90 mg/m². On days 2 to 5 administer 90 mg/m² every 12 hours. The total dose is 1010 mg/m² over a five day period.

The oral bolus dose could be anywhere from 100 to 500 mg/m².

In addition to twice per day dosage, other preferable dosing schedules include thrice per day and four times per day (with or without an initial oral bolus dose.

Temozolomide may be administered orally in capsule form wherein it is admixed with conventional pharmaceutical carriers. Preferred temozolomide capsule formulations are:

| Ingredient | mg/Capsule | | | |
|---|---|---|---|---|
| temozolomide | 5 | 20 | 100 | 250 |
| Anhydrous Lactose NF | 132.8 | 182.2 | 175.7 | 154.3 |
| Sodium Starch Glycolate NF | 7.5 | 11.0 | 15.0 | 22.5 |
| Colloidal Silicon Diozide NF | 0.2 | 0.2 | 0.3 | 0.7 |
| Tartaric Acid NF | 1.5 | 2.2 | 3.0 | 9.0 |
| Steric Acid NF | 3.0 | 4.4 | 6.0 | 13.5 |
| Capsule Size* | 3 | 2 | 1 | 0 |

*White opaque, preservative-free, two-piece hard gelatin capsules

After a period of about 28 to 42 days, or about 28 to 35 days, or more preferably 28 days, from the first day of temozolomide administration, another administration cycle may be performed, with temozolomide being re-administered on day one and on each subsequent day of the administration period.

The treatment cycles may be continued until a disease progression or until intolerable side effects are encountered. The dosage may be decreased, if intolerable side effects or hematologic toxicity are encountered.

A common, but tolerable side effect of both temozolomide is nausea and vomiting. This can be alleviated by administering an anti-emetic in conjunction with the temozolomide. It is preferred that the anti-emetic Ondansetron be given p.o. in a dose of about 8 mg about 30 minutes before temozolomide administration. Of course other anti-emetics such as Hasaldol, Benadryl, and Ativan may also be used as needed.

Of course, other forms of administration of temozolomide, as they become available, are contemplated, such as by IV injection or infusion, intrathecally, by sustained release dosage form, syrup, suppository, transdermal, nasal spray, etc. Any form of administration will work so long as the proper dosage is delivered without destroying the temozolomide.

The effectiveness of treatment may be determined by controlled clinical trials. Patients having a cancer treatable by this invention with measurable or evaluable tumors will be included in the study. A measurable tumor is one that can be measured in at least two dimensions such as a lung tumor surrounded by aerated lung, a skin nodule, or a superficial lymph node. An evaluable tumor is one that can be measured in one dimension such as a lung tumor not completely surrounded by aerated lung or a palpable abdominal or soft tissue mass that can be measured in one dimension. Tumor markers which have been shown to be highly correlated with extent of disease will also be considered to measure for the presence of an evaluable disease. Examples of such tumor markers are PSA for prostate cancer, CA-125 for ovarian cancer, CA-15-3 for breast cancer, etc.

The tumor will be measured or evaluated before and after treatment by whatever means provides the most accurate measurement, such as CT scan, MRI scan, Ultrasonography, etc. New tumors or the lack thereof in previously irradiated fields can also be used to assess the anti-tumor response. The criteria for evaluating response will be similar to that of the WHO Handbook of Reporting Results of Cancer Treatment, WHO Offset Publication 1979, 49-World Health Organization, Geneva. The following results are defined for uni- and bi-dimensionally measurable tumors.

Complete response: means complete disappearance of all clinically detectable malignant disease as determined by two observations not less than four weeks apart.

Partial Response means the following: (a) for bidimensionally measurable tumors, a decrease of at least 50% in the sum of the products of the largest perpendicular diameters of all measurable tumors as determined by two observations not less than four weeks apart. (b) for unidimensionally measurable tumors, a decrease by at least 50% in the sum of the largest diameters of all tumors as determined by two observations not less than four weeks apart. In cases where the patient has multiple tumors, it is not necessary for all tumors to have regressed to achieve a partial response as defined herein, but no tumor should have progressed and no new tumor should appear.

Stable disease means: (a) for bidimensionally measurable tumors, less than a 50% decrease to less than a 25% increase in the sum of the products of the largest perpendicular diameters of all measurable tumors. (b) for unidimensionally measurable tumors, less than a 50% decrease to less than a 25% increase in the sum of the diameters of all tumors. For (a) and (b) no new tumors should appear.

Progressive disease is defined as an increase of 25% or greater in the product of the largest perpendicular diameters for at least one bidimensionally measurable tumor, or an increase of 25% or greater at least one unidimensionally measurable tumor, or appearance of a new lesion.

For patients having both uni- and bi-dimensionally measurable tumors, the overall response will be determined in accordance with the following table.

| Response in bidimensionally measurable disease | Response in unidimensionally measurable disease | Overall Response |
|---|---|---|
| PD | any | PD |
| Any | PD | PD |
| SD | SD or PR | SD |
| SD | CR | PR |
| PR | SD or PR or CR | PR |
| CR | SD or PR | PR |
| CR | CR | CR |

Abbreviations: PD: Progressive Disease
  CR: Complete Response
  PR: Partial Response
  SD: Stable Disease Of course elimination or alleviation of other known signs or symptoms of advanced cancer, especially those listed previously can also be used to evaluate the effectiveness of this invention.

The cancers should be evaluated, i.e. tumors measured, etc., no more than 14 days before the start of the treatment. These cancers should be reevaluated about 28 days after day 1 of administration of the first dose of temozolomide. Twenty eight days after this initial administration another administration and evaluation may be performed. The treatment cycles and evaluations may be continued until disease progression or unacceptable toxicity is encountered.

We claim:

1. A method for treating melanoma, high grade glioma, glioblastoma, lung cancer, breast cancer, testicular cancer, colon and rectal cancers, carcinomas, sarcomas, lymphomas, leukemias, and mycosis fungoides in a patient in need of such treating said method consisting of administering more than once per day temozolomide and an antiemetic to said patient, wherein the temozolomide is present in 500–1,200 mg per $m^2$ based on the patient's body surface area and the antiemetic is administered orally in an amount of about 8 mg about 30 minutes prior to administering said temozolomide.

2. The method of claim 1 wherein the temozolomide and the antiemetic are administered over a period of from 2 to 28 days.

3. The method of claim 2 wherein the temozolomide is administered over a period of from 4 to 7 days.

4. The method of claim 3 wherein the temozolomide is administered over a period of 5 days.

5. The method of claim 2 wherein after a period of 28 to 42 days after the first day of the temozolomide and antiemetic administration period, the temozolomide and antiemetic administrations are repeated.

6. The method of claim 4 wherein after a period of 28 days after the first day of the temozolomide and antiemetic administration period, the temozolomide and antiemetic administrations are repeated.

7. The method of claim 1 wherein the temozolomide is administered daily for at least 6 weeks at a dosage of 50 to 100 $mg/m^2$/day.

8. The method of claim 7 wherein the dosage of temozolomide is 75 $mg/m^2$/day.

9. The method of any one of claim 1 wherein the temozolomide and the antiemetic is administered twice per day.

10. The method any one of claim 1 wherein the temozolomide and the antiemetic is administered three times per day.

11. The method of claim 1 wherein the temozolomide and the antiemetic is administered four times per day.

12. The method of any one of claim 1 wherein an initial oral bolus dose of from 100 to 500 $mg/m^2$ of temozolomide is administered.

* * * * *